US008704159B2

(12) United States Patent
DiFoggio

(10) Patent No.: US 8,704,159 B2
(45) Date of Patent: Apr. 22, 2014

(54) METHOD AND APPARATUS FOR ESTIMATING A DOWNHOLE FLUID PROPERTY USING A CHARGED PARTICLE DENSITOMETER

(75) Inventor: Rocco DiFoggio, Houston, TX (US)

(73) Assignee: AT&T Intellectual Property I, LP, Atlanta, GA (US)

( * ) Notice: Subject to any disclaimer, the term of this patent is extended or adjusted under 35 U.S.C. 154(b) by 216 days.

(21) Appl. No.: 13/293,973

(22) Filed: Nov. 10, 2011

(65) Prior Publication Data

US 2013/0119245 A1    May 16, 2013

(51) Int. Cl.
*G01V 5/08* (2006.01)

(52) U.S. Cl.
USPC ...................................... 250/269.1

(58) Field of Classification Search
USPC .................. 250/269.1, 306, 307, 308, 357.1
See application file for complete search history.

(56) References Cited

U.S. PATENT DOCUMENTS

| | | |
|---|---|---|
| 3,043,955 A | 7/1962 | Friedland |
| 3,131,305 A | 4/1964 | Shombert |
| 3,609,478 A | 9/1971 | King |
| 4,244,223 A | 1/1981 | Geiger |
| 4,490,609 A | 12/1984 | Chevalier |
| 5,049,744 A | 9/1991 | Johnson |
| 5,212,385 A | 5/1993 | Jones |
| 5,306,909 A | 4/1994 | Jones et al. |
| 5,331,155 A | 7/1994 | Blauch |
| 5,423,205 A | 6/1995 | Farchone |
| 5,457,322 A | 10/1995 | Kitaguchi |
| 5,689,540 A | 11/1997 | Stephenson |
| 6,176,323 B1 | 1/2001 | Weirich et al. |
| 6,228,664 B1 | 5/2001 | Bronson et al. |
| 6,318,463 B1 | 11/2001 | Fehrmann |
| 7,075,062 B2 | 7/2006 | Chen et al. |
| 7,221,514 B2 | 5/2007 | Venema et al. |
| 7,368,723 B2 | 5/2008 | Whitehead et al. |
| 7,507,952 B2 | 3/2009 | Groves |
| 7,542,543 B2 | 6/2009 | Shampine |
| 7,609,380 B2 | 10/2009 | Vannuffelen et al. |
| 2010/0236776 A1 | 9/2010 | Spross et al. |
| 2012/0175510 A1* | 7/2012 | Zhou et al. ................ 250/255 |
| 2013/0118248 A1* | 5/2013 | Difoggio ................ 73/152.05 |

* cited by examiner

*Primary Examiner* — David Porta
*Assistant Examiner* — Hugh H Maupin
(74) *Attorney, Agent, or Firm* — G. Michael Roebuck

(57) ABSTRACT

An apparatus, system and method are disclosed for estimating a property of a fluid downhole, the apparatus including but not limited to a carrier that is conveyable in a borehole; a test cell carried by the carrier for capturing a fluid downhole; a fluid channel immersed in the fluid downhole, the fluid channel having a first wall and a second wall, wherein the first wall faces the second wall; at least on charged particle source placed at location along the first wall of the fluid channel; and at least one charged particle detector placed at a location along the second wall of the fluid channel, wherein the at least one radioactive detector is in positioned to be in particle communication with the at least one of the charged particle source.

16 Claims, 7 Drawing Sheets

METHOD AND APPARATUS FOR ESTIMATING A DOWNHOLE FLUID PROPERTY USING A CHARGED PARTICLE DENSITOMETER

CROSS-REFERENCE TO RELATED APPLICATIONS

None
Not Applicable

BACKGROUND

1. Technical Field

The present disclosure generally relates to well bore tools and in particular to an apparatus and methods for using charged particles downhole for estimating density of downhole

2. Background Information

Oil and gas wells have been drilled at depths ranging from a few thousand feet to as deep as 5 miles. Wireline and drilling tools often incorporate various detectors, instruments and control devices in order to carry out downhole operations. These operations may include formation testing, fluid analysis, and tool monitoring and control. In the oil and gas industry, formation testing tools have been used for monitoring formation pressures along a wellbore in a hydrocarbon bearing formation or reservoir, obtaining formation fluid samples from the wellbore and predicting performance of the reservoirs around the wellbore. Such formation testing tools typically contain an elongated body having an elastomeric packer that is sealingly urged against the zone of interest in the wellbore to collect formation fluid samples in storage chambers placed in the tool.

During drilling of a wellbore, a drilling fluid ("mud") is used to facilitate the drilling process and to maintain a pressure in the wellbore greater than the fluid pressure in the formations surrounding the wellbore. This is particularly important when drilling into formations where the pressure is abnormally high. If the fluid pressure in the borehole drops below the formation pressure, there is a risk of blowout of the well. As a result of this pressure difference, the drilling fluid penetrates into or invades the formations for varying radial depths (referred to generally as invaded zones) depending upon the types of formation and drilling fluid used. The formation testing tools retrieve formation fluids from the desired formations or zones of interest, test the retrieved fluids to ensure that the retrieved fluid is substantially free of mud filtrates, and collect such fluids in one or more test cells associated with the tool. The collected fluids are brought to the surface and analyzed to determine properties of such fluids and to determine the condition of the zones or formations from where such fluids have been collected.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

An apparatus, system and method are disclose for estimating a property of a fluid downhole, the apparatus including but not limited to a carrier that is conveyable in a borehole; a test cell carried by the carrier for capturing a fluid downhole; a fluid channel immersed in the fluid downhole, the fluid channel having a first wall and a second wall, wherein the first wall faces the second wall; a quantity of charged particle sources placed at locations along the first wall of the fluid channel; and a quantity of charged particle detectors placed at locations along the second wall of the fluid channel, wherein at least one of the radioactive detectors is positioned to be in particle communication with at least one of the charged particle sources.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals.

DETAILED DESCRIPTION

Figure 1:
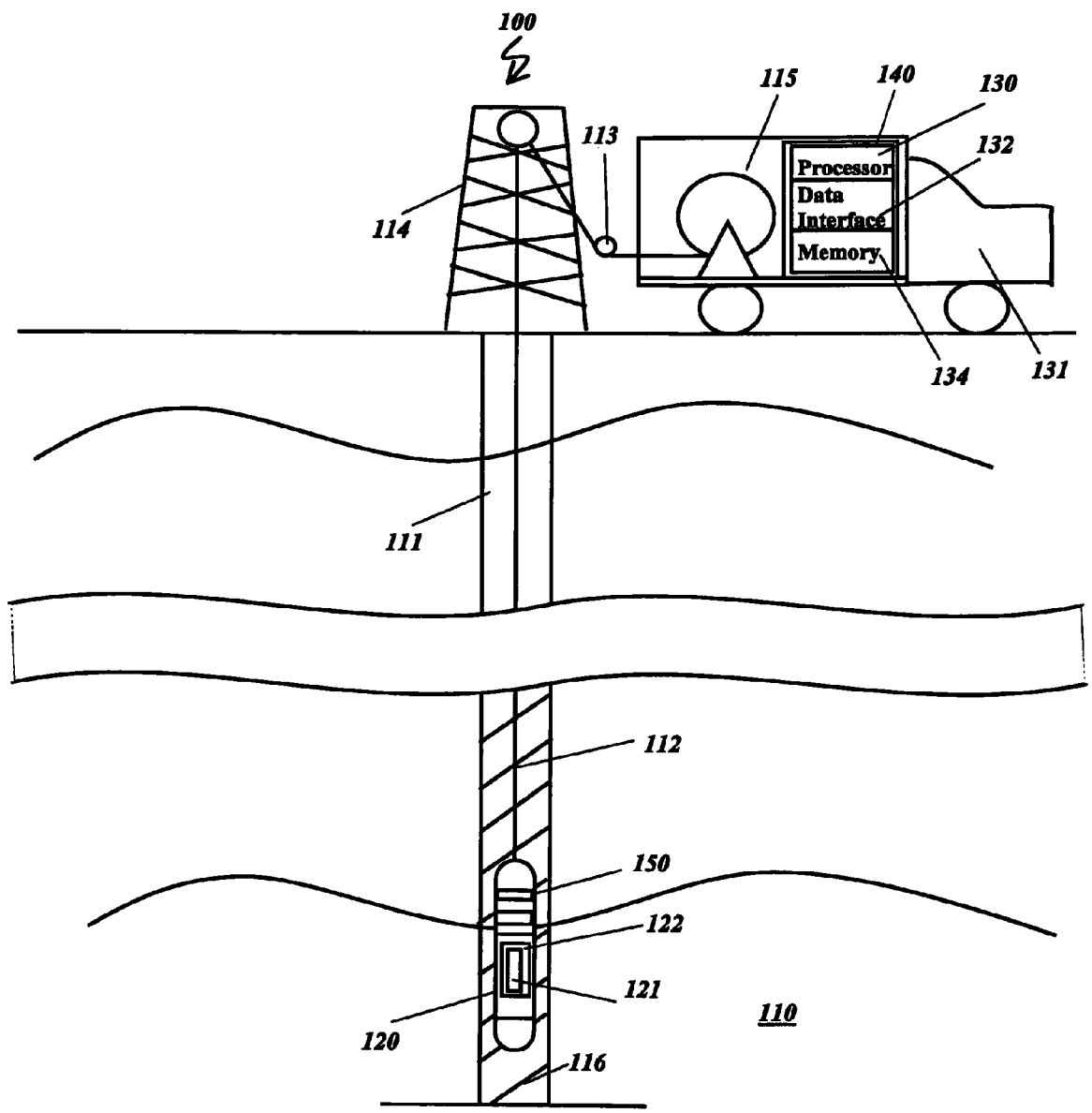
FIG. 1 is a schematic illustration of a well logging system that includes a tool made according to one embodiment of the disclosure, that utilizes a charged particle densitometer made according to one embodiment of the disclosure, which logging tool is shown conveyed in a wellbore for estimating a property of the fluid obtained from a formation surrounding the wellbore.

The present disclosure uses terms, the meaning of which terms will aid in providing an understanding of the discussion herein. As used herein, high temperature refers to a range of temperatures typically experienced in oil production well boreholes. For the purposes of the present disclosure, high temperature and downhole temperature include a range of temperatures from about 70 degrees C. to about 300 degrees C.

The term "carrier" as used herein means any device, device, component, combination of devices, media and/or member that may be used to convey, house, support or otherwise facilitate the use of another device, device component, combination of devices, media and/or member. Exemplary non-limiting carriers include wire lines and drill strings of the coiled tube type, of the jointed pipe type and any combination or portion thereof.

A "downhole fluid" as used herein includes any gas, liquid, flowable solid and other materials having a fluid property. A downhole fluid may be natural or man-made and may be transported downhole or may be recovered from a downhole location. Non-limiting examples of downhole fluids include but are not limited to drilling fluids, return fluids, formation fluids, production fluids containing one or more hydrocarbons, oils and solvents used in conjunction with downhole tools, water, brine and combinations thereof.

"Processor" as used herein means any device that transmits, receives, manipulates, converts, calculates, modulates, transposes, carries, stores or otherwise utilizes well information and electromagnetic information, discussed below. In several non-limiting aspects of the disclosure, a processor includes but is not limited to a computer that executes programmed instructions stored on a tangible non-transitory computer readable medium for performing various methods.

Portions of the present disclosure, detailed description and claims may be presented in terms of logic, software or software implemented illustrative embodiments that are encoded on a variety of tangible non-transitory computer readable storage media including, but not limited to tangible non-transitory machine readable media, program storage media or computer program products. Such media may be handled, read, sensed and/or interpreted by an information processing device. Those skilled in the art will appreciate that such media may take various forms such as cards, tapes, magnetic disks (e.g., floppy disk or hard disk drive) and optical disks (e.g., compact disk read only memory ("CD-ROM") or digital versatile (or video) disk ("DVD")). Any embodiment disclosed herein is for illustration only and not by way of limiting the scope of the disclosure or claims.

A particular embodiment of a charged particle densitometer is disclosed that is useful for determining density of a fluid downhole in boreholes exceeding 200 degrees centigrade. In a particular embodiment provides a radioactive or charged particle (the terms "charged particle" and "radioactive" are used synonymously herein) source emitting charged particles in a borehole exceeding 300 degrees centigrade to measure fluid density of a fluid downhole. A radioactive source is provided along with a radioactive detector separated by a fixed distance. A fluid channel filled with the fluid downhole is positioned between the radioactive source and the detector. For a "thin" radioactive source emitting substantially a single energy charged particles (monoenergetic particles), the detector measures average energy loss. For a "thick" radioactive source, emitting charged particles at many different energy levels, the detector measures a count rate above some threshold. The detector response is proportional to the product of the fluid density with the separation distance.

The radioactive source in one particular embodiment is an alpha particle source, such as Americium 241. Other alpha particle sources can be used based on the desired energy level of the charged particles, the expected density of the downhole fluid and a width of a fluid channel in which the downhole fluid is tested in situ and the range of charged particles in the fluid in the fluid channel. In another particular embodiment a plurality of charged particle densitometers, each using a different charged particle source material to provide increased dynamic range of density measurements downhole for various fluids. In a particular embodiment a diamond detector is provided for used for alpha particle detection. The diamond detector is a wide band gap semiconductor that works well above 300 degrees centigrade.

The range of a 5.5 MeV alpha particle in air is approximately 4 cm at room temperature and 1 atmosphere but is only about 40 microns in water because of the water's much higher mass density (1.0 g/cc). In a particular embodiment, such as for downhole fluids, a fluid channel is etched into a substrate surface. The fluid channel in one embodiment is about 500 microns deep and about 40 microns wide. The 40 micron wide fluid channel forms a first and second wall running parallel relative to each other along the length of the fluid channel. In another embodiment, the fluid channel is divergent, wherein the first and second wall forms a divergent angle relative to each other wherein the first and second wall are not parallel relative to each other, but form a divergent angle forming a fluid channel being wider at on end than at the other end. In another particular embodiment the fluid channel is coated with nonstick coating such as a 4 nm thick ceramic coating such as an oxyfluoride coating, which in a particular embodiment is at least one of hydrophobic, lipophobic, hard, and chemically resistant to solvents, acids, and bases.

Some examples of alpha particle decays and half life include but are not limited to those in Table 1.

TABLE 1

| Isotope | Half Life | Alpha Energy (MeV) |
|---------|-----------|--------------------|
| 208 Po  | 2.898 years | 5.1149 |
| 222 Rn  | 3.8235 years | 5.48948 |
| 241 Am  | 432.2 years | 5.5445, 5.48556, 5.44280 |

It is well known that the range (maximum distance) that a charged particle can travel in a medium is indicative of the density of that medium. Thus, by measuring this distance for a charged particle traveling in a medium, such as a fluid, one has a measure indicative of the density of that fluid. Sometimes equations for a medium-independent, "normalized range" are given in reference texts and it has units of density times distance or $g/cm^3 * cm = g/cm^2$ in which case the density of the fluid is calculated as the normalized range ($g/cm^2$) divided by the actual range (cm). A charged particle moving through a neutral medium will interact electromagnetically with both the electrons and nuclei of the medium. The electromagnetic interactions with the nuclei cause scattering and are seen as small and occasionally small changes in directions. The interactions with the electrons are far more frequent and are seen as a fairly steady loss of kinetic energy. Therefore, the density of a fluid can be estimated by measuring the presence or absence of a signal along an array of particle detectors immersed in the fluid and situated at different distances from their corresponding radioactive sources. Somewhere along this array of source and detector pairs on opposite walls of a wedge-shaped channel that holds the fluid, the path through the fluid becomes too long to pass any charged particles. Then, we know that the particle range must be greater than the largest distance between a source-detector pair for which some particles were detected but less than the smallest distance between a source-detector pair for which no signal was detected. Alternatively, we can measure the energy of the charged particles striking each detector before and after the channel is filled with fluid, and, from the drop in detected particle energy with increasing fluid path length, we can estimate the fluid density.

The well known Bethe formula below relates energy loss per unit length to particle energy, the density of the medium being traversed by the particle, and various physical constants. The particle range is obtained by integrating dE/(dE/dx) from the particle energy to zero.

$$\frac{dE}{dx} = -\frac{1}{(4\pi\varepsilon_0)^2} \frac{4\pi e^4 z^2 NB}{m_e v^2}$$

where
    e=charge on electrons (coulombs).
    z=atomic number of moving particle.
    N=the number of atoms/unit volume (meter$^{-3}$).
    $m_e$=mass of electron (kg).
    v=velocity of moving particle (meter/sec).
    E=kinetic energy of the moving particle (joules).
    x=distance traveled by the particle (meter).
    $\varepsilon_0$=permittivity of free space.
    $1/(4\pi\varepsilon_0)^2$=8.988×10$^9$ Newton meter$^2$/coulomb$^2$.
    B=Atomic stopping number (dimensionless).

An easier approach is to use various empirical formulas for normalized range such as the Katz and Penfold (Rev. Mod. Phys. 24, [1952], p. 28) formulas for beta particles.

$$R_{max}[g/cm2]=0.412\, E_\beta^{1.265-0.0954\, ln(E\beta)}\; 0.01 \leq E_\beta \leq 2.5\, MeV$$

$$R_{max}[g/cm2]=0.530\, E_\beta - 0.106\; E_\beta > 2.5\, MeV$$

Similarly, one can use the empirical formulas for alpha particle range in air given in Cember (Introduction to Health Physics, 3$^{rd}$ ed. McGraw-Hill, 1996, p. 132), namely:

$$R_{air}[cm]=0.56\, Ea\; Ea<4\, MeV$$

$$R_{air}[cm]=1.24\, Ea-2.62\; 4 \leq Ea \leq 8\, MeV$$

To estimate the range for alpha particles in some other medium, one can apply the Bragg-Kleeman rule (*Philosophical Magazine* 10, 358 [1905]) for the ratio of the ranges in the two media, where $\rho_1$ and $\rho_2$ are the densities of the first and second media and $M_1$ and $M_2$ are the effective atomic masses of the two media. For a compound or mixture, the effective atomic mass can be calculated from the atomic or weight fractions of the constituents as shown below.

$$R_1/R_2=(\rho_2/\rho_1)sqrt(M_1/M_2)$$

$$Sqrt(M_{eff})=\Sigma_i \gamma_i\, Sqrt(M_i)\; \text{where } \gamma_I \text{ is the atomic fraction}$$

$$1/Sqrt(M_{eff})=\Sigma_i[\omega_i/Sqrt(M_i)]\; \text{where } \omega_I \text{ is the weight fraction}$$

For crude oil, there is roughly a 2:1 ratio of hydrogen to carbon so Sqrt($M_{eff}$) is approximately (⅔)Sqrt(1)+(⅓)Sqrt(12)=5.75.

FIG. 1 is a schematic representation of a wireline formation testing system 100 for estimating a property of a downhole fluid. FIG. 1 shows a wellbore 111 drilled in a formation 110. The wellbore 111 is shown filled with a drilling fluid 116, which is also is referred to as "mud" or "wellbore fluid." The term "connate fluid" or "natural fluid" herein refers to the fluid that is naturally present in the formation, exclusive of any contamination by the fluids not naturally present in the formation, such as the drilling fluid. Conveyed into the wellbore 111 at the bottom end of a wireline 112 is a formation evaluation tool 120 that includes but is not limited to an analysis module 150 and a charged particle densitometer 121 made according to one or more embodiments of the present disclosure for in-situ estimation of a property of the fluid withdrawn from the formation. The formation evaluation tool 120 acts a carrier for the charged particle densitometer 121 and a test cell 122. Exemplary embodiments of various formation evaluation tools are described in more detail in reference to FIGS. 3-7.

The wireline 112 typically is an armored cable that carries data and power conductors for providing power to the tool 120 and a two-way data communication link between a tool processor in the analysis module 150 and a surface controller 140 placed in surface unit, which may be a mobile unit 111, such as a logging truck 131. The surface controller and analysis module 150 each included but are not limited to a processor 130, data interface 132 and non-transitory computer readable media 134.

The wireline 112 typically is carried from a spool 115 over a pulley 113 supported by a derrick 114. The controller 140 and analysis module 150 are each in one aspect, a computer-based system, which may include one or more processors such a microprocessor, that may include but is not limited to one or more non-transitory data storage devices, such as solid state memory devices, hard-drives, magnetic tapes, etc.; peripherals, such as data input devices and display devices; and other circuitry for controlling and processing data received from the tool 120. The surface controller 140 and analysis module 150 may also include but is not limited to one or more computer programs, algorithms, and computer models, which may be embedded in the non-transitory computer-readable medium that is accessible to the processor for executing instructions and information contained therein to perform one or more functions or methods associated with the operation of the formation evaluation tool 120.

The test cell 122 may include but is not limited to a downhole fluid sample tank and a flow line 211 for downhole fluid to flow into the sample tank. At least a portion of the charged particle densitometer 121 is immersed in the downhole fluid in the test cell 122 and used for in situ or surface analysis of the downhole fluid, including but not limited to estimating viscosity and density of the downhole fluid. The test cell may be any suitable downhole fluid test cell in accordance with the disclosure. Non-limiting examples of a test cell include but are not limited to a downhole fluid sample chamber and a downhole fluid flow line. Additional downhole test device for estimating a property of the downhole fluid may be included in the formation evaluation tool 120, any test device may be included in accordance with disclosure, including but not limited to nuclear magnetic resonance (NMR) spectrometers, pressure, temperature and electromechanical resonators, such as electrically drive piezoelectric resonators.

Figure 2:
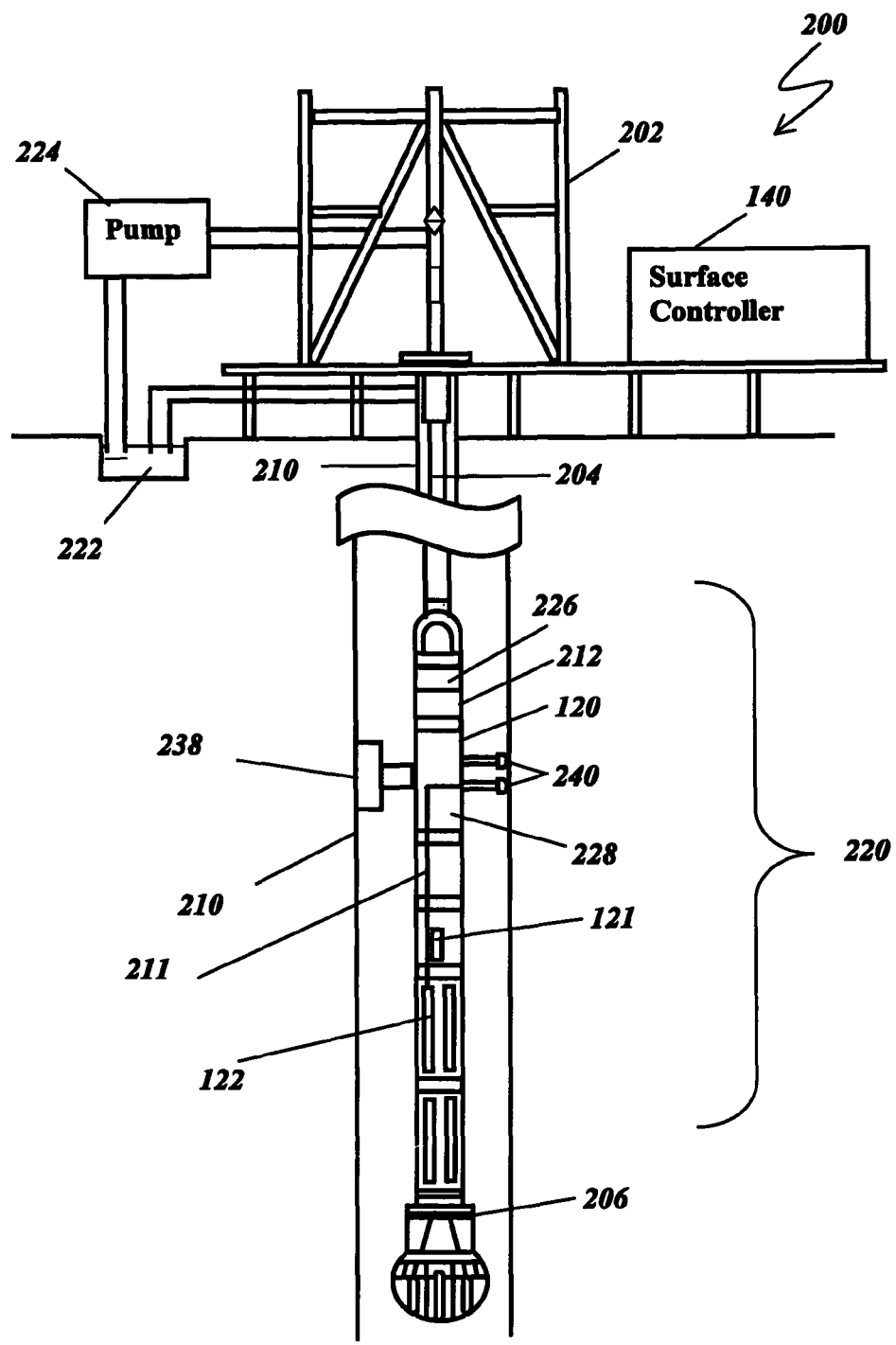
FIG. 2 is a schematic illustration of an exemplary well drilling tool that utilizes a charged particle densitometer made according to one embodiment of the disclosure, which tool may be placed at a selected location in the wellbore for in-situ analysis of the fluid being withdrawn from the formation.

FIG. 2 depicts a non-limiting example of a drilling system 200 in a measurement-while-drilling (MWD) arrangement according to one embodiment of the disclosure. A derrick 202 supports a drill string 204, which may be a coiled tube or drill pipe. The drill string 204 may carry a bottom hole assembly (BHA) 220 and a drill bit 206 at a distal end of the drill string 204 for drilling a borehole 210 through earth formations. Drilling operations according to several embodiments may include pumping drilling fluid or "mud" from a mud pit 222, and using a circulation system 224, circulating the mud through an inner bore of the drill string 204. The mud exits the drill string 204 at the drill bit 206 and returns to the surface through an annular space between the drill string 204 and inner wall of the borehole 210.

In the non-limiting embodiment of FIG. 2, the BHA 220 may include a formation evaluation tool 120, a power unit 226, a tool processor 212 and a surface controller 140. Any suitable power unit may be used in accordance with the disclosure. Non-limiting examples of suitable power units include but are not limited to a hydraulic, electrical, or electro-mechanical and combinations thereof. The tool 120 may carry a fluid extractor 228 including a probe 238 and opposing feet 240. In several embodiments to be described in further detail below, the tool 120 includes but is not limited to a downhole charged particle densitometer 121. A flow line 211 connects fluid extractor 228 to test cell 122 and charged particle densitometer 121. The charged particle densitometer may be used in either the while-drilling embodiments or in the wireline embodiments for in situ or surface estimation of a property of the downhole fluid.

Those skilled in the art with the benefit of the present disclosure will recognize that the several embodiments disclosed are applicable to a formation fluid production facility without the need for further illustration. The several examples described below and shown in FIG. 3-7 may be implemented using a wireline system as described above and shown in FIG. 1, may be implemented using a while-drilling system as described above and shown in FIG. 2 or may be implemented in a production facility to monitor production fluids.

In a particular embodiment a plurality of radioactive sources and radioactive detectors are provided along a divergent fluid channels so that multiple charged particle range measurements are made for a fluid in the fluid channel at varying distances. In another embodiment, at least one of the detectors and one of the sources are movable relative to each other so that the distance between them varies and the width of a fluid channel between them varies. In a particular embodiment, a least squares fit of the multiple charged particle range measurements is applied to the formula calculating density from charge particle range, thereby improving the accuracy of the fluid density calculation. In another embodiment, each source is a vertical array of sources and each detector is a vertical array of detectors spaced along the horizontal fluid path. Multiple sources and detectors not only enable improving the accuracy of fluid density calculations, they also help reduce false measurements caused by a particle displacing or blocking fluid in the fluid channel between a particular single charged particle source and charged particle detector pair.

The divergent fluid channel provides increased dynamic range so that when a density for a fluid in the fluid channel changes and the range of particles in the fluid changes, the varying distance of the divergent fluid channel helps to accommodate the changes in range by providing a varying range of measurements along the divergent fluid channel. In another embodiment an adjustable fluid channel width is provided between movable walls of the fluid channel. In another embodiment a divergent calibration channel is provided to detect charged particles through a known medium downhole. The calibration channel can also be an adjustable width calibration channel formed between movable walls mounted on one more positioners. The calibration measurements are useful in monitoring charged particle source deterioration for source having relatively short half lives, for example, 5 years, eliminating the need to recall the tool for such measurements. In a particular embodiment, the calibration channel is filled with a calibration medium such as silicon. In another particular embodiment, the fluid channel is etched into a silicon block. The calibration data indicates how many charged particles are emitted by the source and travel through a source with a known range for the particular alpha particle source.

In another embodiment, the dynamic range of the divergent fluid channel and divergent calibration channel are useful in successively filtering out charged particle measurements for the various energy charged particles in a broad band radioactive source wherein the different energy charged particle have different ranges in the fluid in the divergent fluid path and the divergent calibration path filled with a calibration medium. The multiple widths of the divergent channel enable measurement and build up of a distribution for different energy charged particle in the broadband charged particle source.

Those skilled in the art with the benefit of the present disclosure will recognize that the several embodiments disclosed are applicable to a formation fluid production facility without the need for further illustration. The several examples described below and shown in FIG. 3-7 may be implemented using a wireline system as described above and shown in FIG. 1 may be implemented using a while-drilling system as described above and shown in FIG. 2 or may be implemented in a production facility to monitor production fluids.

Figures 3A, 3B:
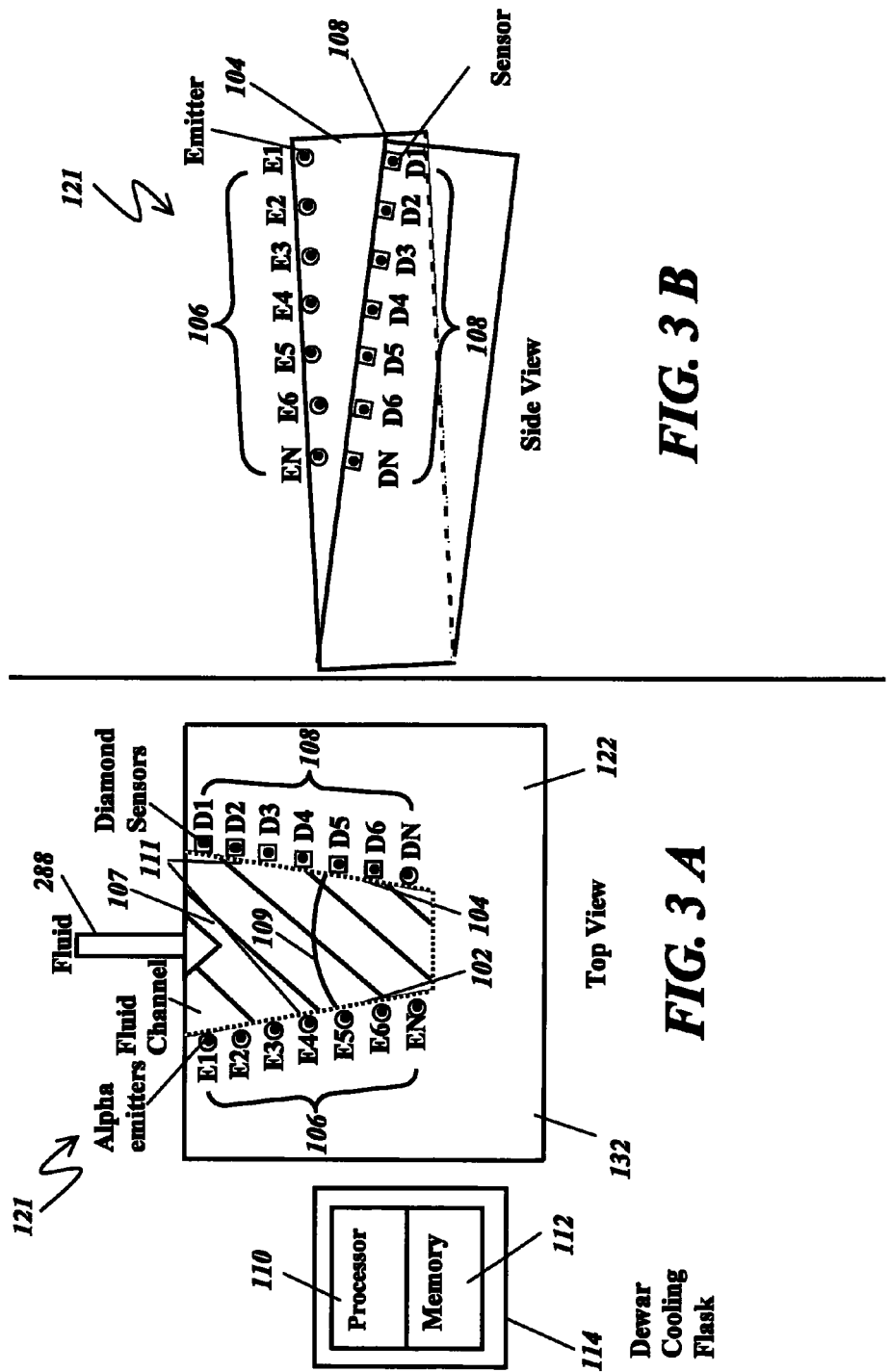
FIG. 3 is a schematic illustration of a particular illustrative embodiment of a charged particle densitometer according to the disclosure.

FIGS. 3A and 3B show a schematic diagram of a module of the charged particle densitometer 121 for use in a downhole tool, such as the tool 120. It is shown to include certain elements or components of the charged particle densitometer 121 made according to one exemplary embodiment. The charged particle densitometer 121 may be utilized in a wireline tool, such as shown in FIG. 1 or in a drilling assembly used for drilling a wellbore shown in FIG. 2. A portion 431 of the downhole fluid 288 is passed into or through a test cell 122 as a fluid downhole. The test cell 122 may hold the fluid downhole or may allow it to pass there through.

Turning now to FIG. 3A, FIG. 3A depicts an illustrative embodiment of a downhole densitometer is illustrated. As shown in FIG. 3, a test cell 122 carried by the carrier for capturing a fluid downhole; a divergent width fluid channel 107 etched in to a substrate 132 and immersed in the downhole fluid 288 downhole so that the downhole fluid fills the divergent width fluid channel, the divergent width fluid channel having a first wall 102 and a second wall 104, wherein the first wall faces the second wall and is placed at a divergent angle 109 relative to the second wall; a quantity, N of alpha particle radioactive sources 106 placed at linear locations 1 through N along the first wall of the fluid channel; a quantity, N of alpha particle radioactive detectors 108 placed in linear locations 1 through N along the second wall of the fluid channel, wherein each of the radioactive detectors 1 through N is positioned to be in particle communication with a corresponding Nth one of the radioactive sources 1 through N; and a processor 110 in data communication with a non-transient computer readable medium 112 configured to estimate density of the fluid in the fluid channel based on a quantity of alpha particles passing through the fluid in the fluid channel in at least one of the locations, 1 through N. In another embodiment there are a different number of source than detectors. In another embodiment at least one of the radioactive detectors is in particle communication with at least one of the radioactive sources.

In another embodiment there are a different number of sources than there are detectors. The processor and computer readable medium are cooled by a Dewar flask 114 or other cooling system known in the art. In another embodiment the walls 102 and 104 are coated with a non stick coating 111 rated to 300 degrees centigrade. In another embodiment, the radioactive source, detector and coating are rated up to 250 degrees centigrade. FIG. 3B depicts a side view of the densitometer depicted in FIG. 3A.

Figure 4:
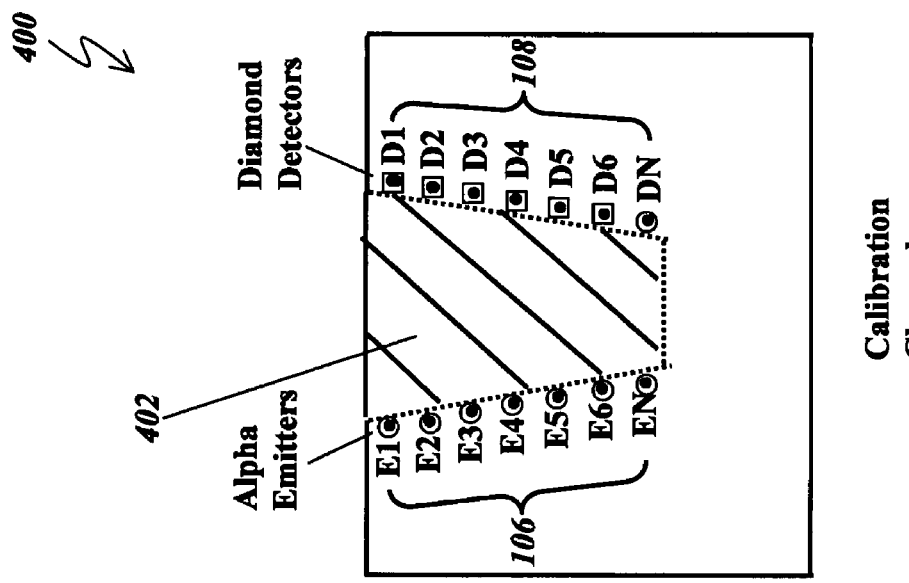
FIG. 4 is a schematic illustration of another particular illustrative embodiment of a charged particle densitometer according to the disclosure.
Figure 5:
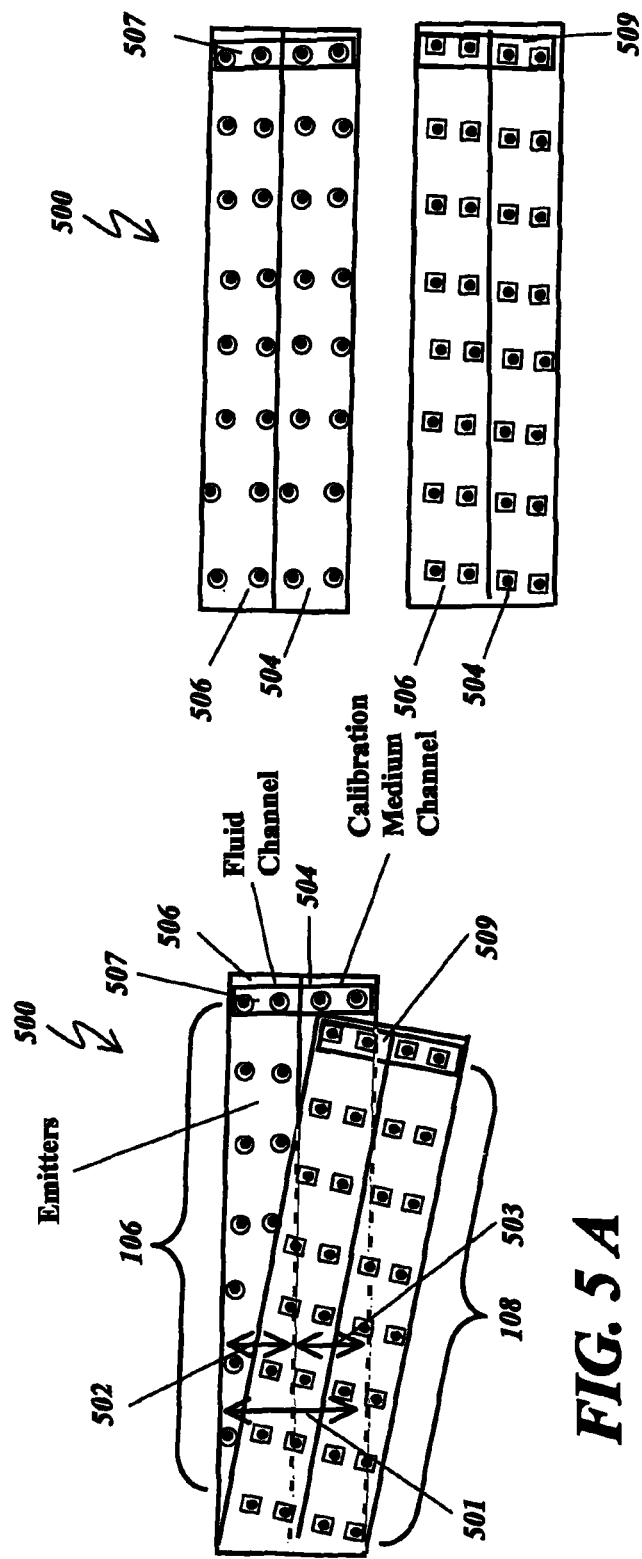
FIG. 5 is a schematic illustration of another particular illustrative embodiment of a charged particle densitometer according to the disclosure.

Turning now to FIG. 4, in another illustrative embodiment 400 a calibration channel is provided. In a particular embodiment, the calibration channel is identical to the fluid channel in FIG. 3, including the alpha particle sources 106 and detectors 108, however, the calibration channel is filled with a calibration medium 402. The calibration medium can be silicon or any medium which allows passage of the charged particles through the calibration medium through at least a portion of the divergent calibration channel. The calibration channel enables detection of charged particles through a known calibration medium at a known distance in the calibration channel. The width of the divergent channel is known for each source and each detector. Thus, one knows the distance a charged particle has traveled across the divergent calibration channel or the divergent fluid channel when the charged particle is detected at a particular detector along a wall of the divergent calibration channel or the divergent fluid channel.

Turning now to FIG. 5A, in another particular embodiment, the fluid channel has a constant depth, D 501 wherein a first portion 504 of the fluid channel has a depth 503 and is filled with a calibration medium and a second portion 506 having depth 502 in the fluid channel is filled with the fluid downhole, wherein each of the N of alpha particle sources 106 further comprise a vertical array 507 of M alpha particle sources, wherein at least one of the M alpha particle sources in an Nth vertical array of alpha particle sources is positioned to emit alpha particles into the calibration medium at the Nth linear location in the fluid channel and another one of the M alpha particle sources in the Nth vertical array is positioned to emit alpha particles into the fluid channel at the Nth linear location in the fluid channel, and wherein each of the N of alpha particle detectors further comprise a vertical array 509 of M alpha particle detectors, wherein at least one of the M alpha particle detectors in an Nth vertical array of alpha particle detectors is positioned to detect the alpha particles passing through the calibration medium in the fluid channel at the Nth linear location and another one of the M alpha particle detectors in the Nth vertical array is positioned to detects alpha particles passing through the fluid channel at the Nth linear location in the fluid channel.

The calibration channel is useful to determine what a reading of emitted particles would be when no fluid is present in the fluid channel. The multiple sources and detectors are useful to provide additional dynamic range for fluids that may have a range between the first gap and the second gap. For example, for a radioactive particle having a range of 40 microns in a particular fluid, the fluid channel having a gap width of 5 to 50 microns would allow measurement of the charged particles passing through fluid at linear positions along the divergent fluid path, for example, at 5, 10, 15, 20, 25, 30, 35, 40 and 50 microns. A parallel fluid gap of 50 microns would register zero charged particles for the source in a fluid having a range of 40 microns. Likewise, the multiple positions along the divergent fluid path enable the densitometer to measure a wide variety of fluids having particle ranges from the first small end of the fluid channel to the second large end of the fluid channel. The fluid channel first narrow gap and second end large gap dimensions can be adjusted for the expected range of the chosen radioactive source in the expected fluid to be measured.

FIG. 5B depicts an illustrative embodiment a front view of each wall of the divergent fluid channels showing the arrays of emitters 507 and the arrays of detectors 509. The radioactive sources can be chosen to emit alpha rays from a source such as Americium. Alpha particles are commonly emitted by all of the larger radioactive nuclei such as uranium, thorium, actinium, and radium, as well as the transuranic elements.

In a particular illustrative embodiment, a silicon sold-state detector is used to measure energy of alpha particles that have passed through from an Am source. The air pressure may be varied so that the alpha particle. The plurality of sources at variable distances along the divergent fluid channel enable a back fit of measurements, using a technique such as a least squares fit to the Bethe formula to improve accuracy of density estimates using an illustrative embodiment of the charged particle densitometer.

Figure 6:
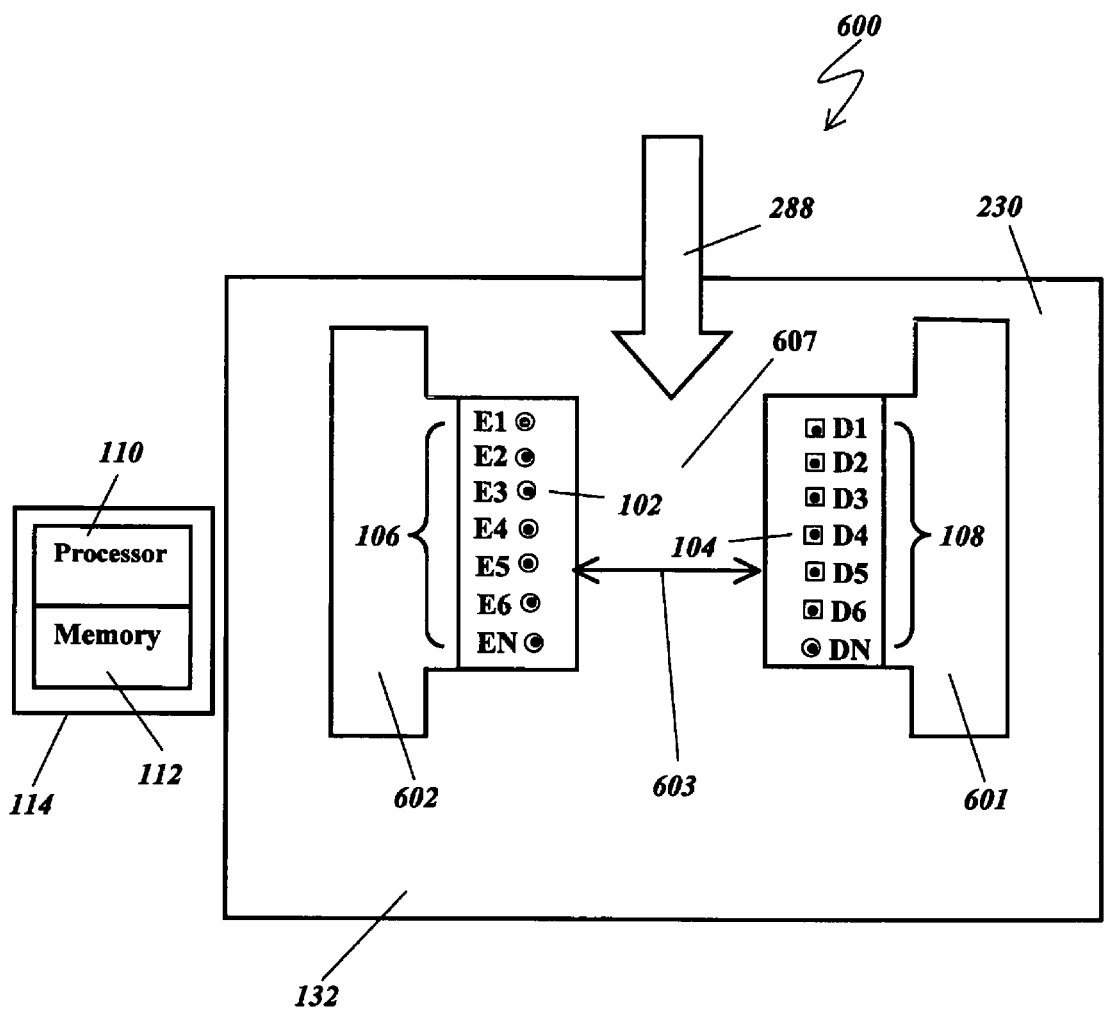
FIG. 6 is a schematic illustration of another particular illustrative embodiment of a charged particle densitometer according to the disclosure.

Turning now to FIG. 6 depicts an illustrative embodiment of a downhole densitometer having an adjustable width fluid channel 607. As shown in FIG. 6, in another non limiting embodiment, a first wall 102 and a second wall 104 form an adjustable width fluid channel for the downhole fluid. The first wall can be formed by etching the wall onto a first section of a medium such as a silicon wafer containing a plurality of charged particle emitters E1-En 106. The first wall of emitters is in physical contact with a first positioner 602. The second wall is etched onto a second section of a medium such as a silicon wafer containing a plurality of detectors D1-Dn. The second medium containing the second wall of sources S1-Sn is in physical contact with a second positioner 601. The second positioner 601 is controlled by processor 110 and is actuated to move the second wall 104 a distance 603 closer to or farther away from the first wall 104.

The distance 603 between the first wall and second determines the width of the adjustable width fluid channel. The first positioner alone, the second positioner alone or the first and second positioners together can be actuated to change the width of the fluid channel. The positioner 601 and 602 can be any mechanical or electromechanical device suitable for adjusting the width of the adjustable width fluid channel between in a range of about 5-100 microns. Wider separations could be achieved for densitometers used for gases in fluid channel. Thus, the divergent fluid channel or the adjustable width fluid channel can have fluid channel widths exceeding 100 microns. Non limiting examples of suitable positioners include but are not limited to piezoelectric device, a piezoelectric stack device and a screw driven micro positioner, that is to say, a positioner that can move a distance with spatial resolution at about the micron level.

Piezoelectric actuators convert electrical energy directly to mechanical energy. They make motion in the sub-nanometer range possible. There are no moving parts in contact with each other to limit resolution. They can cover travel ranges of several 100 μm with resolutions in the sub-nanometer range. Piezo actuators can perform sub-nanometer moves at high frequencies because they derive their motion from solid-state crystalline effects. They have no rotating or sliding parts to cause friction. Stack piezoelectric actuators are the most common and can generate the highest forces. Units with travel ranges up to 500 μm are available. To protect a piezoelectric against destructive external conditions, they are often provided with a metal casing and an integrated preload spring to absorb tensile forces. Piezo tube actuators exploit the radial contraction direction, and are often used in scanning microscopes and micropumps.

In another embodiment, piezoelectric bender and bimorph actuators achieve travel ranges in the millimeter range (despite their compact size) but with relatively low force generation (a few newtons). Shear elements use the inverse piezo-effect shear component and achieve long travel and high force. Guided piezo actuators (1 to 6 axes) are complex nanopositioners with integrated piezo drives and solid-state, friction-free linkages (flexures). They are used when requirements like the following need be met: Extremely straight and flat motion, or multi-axis motion with accuracy requirements in the sub-nanometer or sub-microradian range. In another embodiment, lever amplification of up to 20 times the displacement of the piezo element results in a travel range of several hundred μm. Piezomotors can be used where even longer travel ranges are required. Piezomotors can be divided into two main categories. The motion of ultrasonic piezomotors is based on the friction between parts oscillating with microscopic amplitudes. Linear ultrasonic motors are very compact and can attain high speeds combined with resolutions of 0.1 µm or better. Rotary motors feature high torques even at low rpm. Piezo electric positioners, in the micron and nanometers scale including servomotors for controlling and determining position of the piezoelectric positioner are commercially available from PI (Physik Instrumente) L. P., 16 Albert Street, Auburn, Mass. 01501. Other non limiting examples of the positioner are screw driven positioner and manual positioners, also available from PI.

A test cell 122 carried by the carrier, captures downhole fluid. The downhole fluid is present in the adjustable width fluid channel between walls 102 and 104. The adjustable width fluid channel is immersed in the fluid 288 downhole so that the downhole fluid. The downhole fluid fills the adjustable width fluid channel. As in the examples above, the adjustable width fluid channel has a first wall 102 and a second wall 104, wherein the first wall faces the second wall and is placed at an adjustable distance 603 relative to the second wall. A quantity of alpha particle radioactive sources 106 placed at linear locations along the first wall of the fluid channel; a quantity of alpha particle radioactive detectors 108 placed in locations along the second wall of the fluid channel, wherein each of the radioactive detectors is in positioned to be in particle communication with a corresponding at least one of the radioactive sources. A processor 110 in data communication with a non-transient computer readable medium 112 configured to estimate density of the fluid in the fluid channel based on a quantity of alpha particles passing through the fluid in the fluid channel in at least one of the locations. The positioners, processor and computer readable medium are cooled by a Dewar flask 114 filled or other cooling system known in the art. In another embodiment the walls 104 and 109 are coated with a non stick coating 111 rated to 300 degrees centigrade. The walls are moved until a distance at which no signal is detected is determined. In another embodiment, the radioactive source, detector and coating are rated up to 250 degrees centigrade. The distance between the first wall and the second wall is adjusted by positioners 601 and or 602. A controller 112, including but not limited to a non-transitory computer readable data storage medium 112 and a processor 110, provides a control signal to the positioner to change the distance between the first wall and the second wall. Non limiting examples of the positioner include but are not limited to a piezoelectric device, a piezoelectric stack, and a screw positioner.

Any positioner may be used in accordance with this disclosure. In a particular embodiment, the first wall is stationary and the positioner for the second wall is controlled by processor 110 to move the second wall closer or farther away from the first wall to adjust the width of the adjustable width fluid channel. The width of the adjustable width fluid channel is increased until charged particles from the emitters on the first wall of the adjustable width fluid channel are no longer detected by the detectors on the second wall of the adjustable width fluid channel. This width is then used to estimate the density of the downhole fluid in the adjustable width fluid channel.

In another particular embodiment, the second wall is stationary and the positioner for the first wall is controlled by processor 110 to move the first wall closer or farther away from the second wall to adjust the width of the adjustable width fluid channel. The width of the adjustable width fluid channel is increased until charged particles from the emitters on the first wall of the adjustable width fluid channel are no longer detected by the detectors on the second wall of the adjustable width fluid channel. This width is then used to estimate the density of the downhole fluid in the adjustable width fluid channel.

In another particular embodiment, the first wall and the second are controlled by processor 110 to move the second wall closer or farther away from the first wall to adjust the width of the adjustable width fluid channel. The width of the adjustable width fluid channel is increased until charged particles from the emitters on the first wall of the adjustable width fluid channel are no longer detected by the detectors on the second wall of the adjustable width fluid channel. This width is then used to estimate the density of the downhole fluid in the adjustable width fluid channel.

Figure 7:
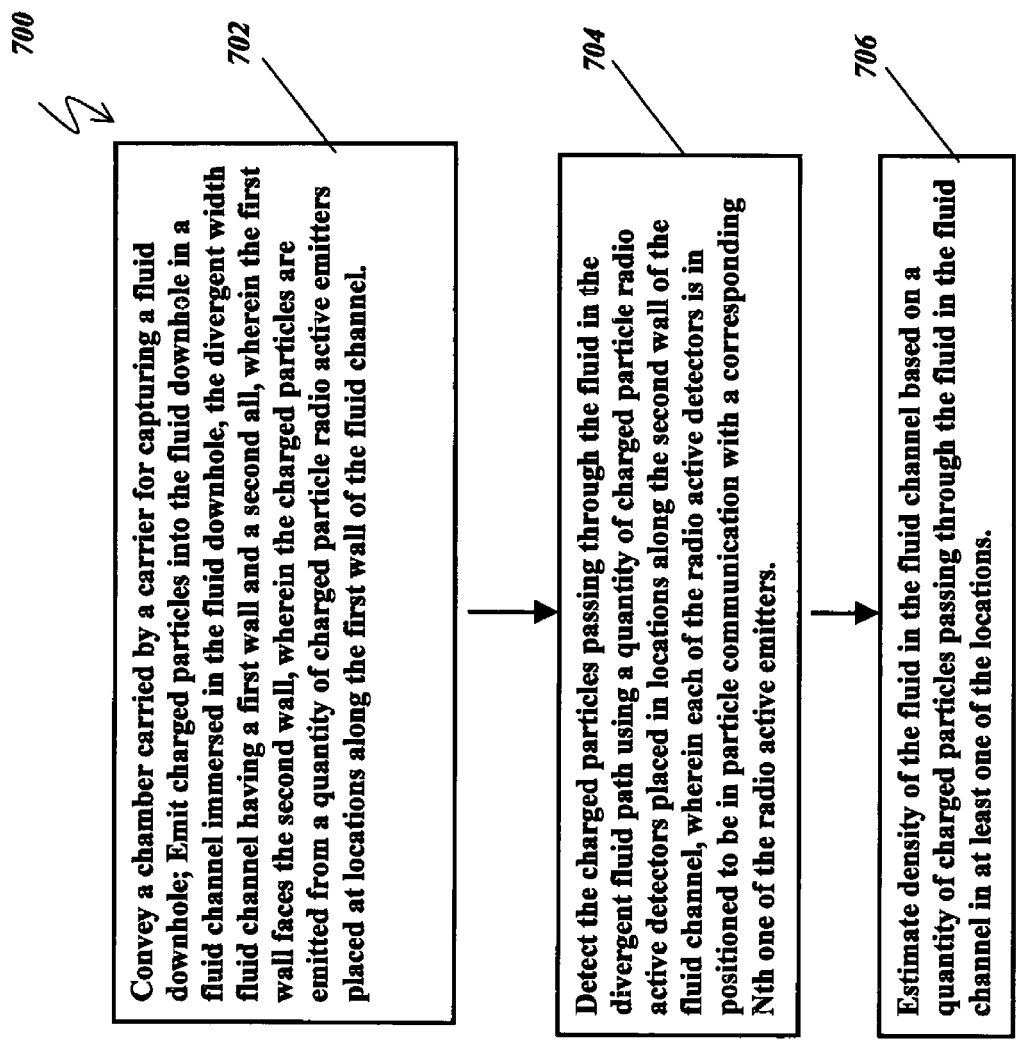
FIG. 7 depicts a flow chart of operations performed in a particular illustrative embodiment.

Turning now to FIG. 7, a flow chart of operations performed in a particular illustrative embodiment is depicted. The flow chart is non-limiting in that more or less operations than those shown in FIG. 7 may be performed and operations, more or less may be performed in an order not shown in FIG. 7. As shown in FIG. 7, in a particular illustrative embodiment, as shown in block 702 operations include but are not limited to conveying a test cell carried by the carrier for capturing a fluid downhole; emitting charged particles into the fluid downhole in a fluid channel immersed in the fluid downhole, the fluid channel having a first wall and a second wall, wherein the first wall faces the second wall, wherein the charged particles are emitted form a quantity of charged particle radioactive sources placed at locations along the first wall of the fluid channel. As shown in block as shown in block 704 operations further include but are not limited to detecting the charged particles passing through the fluid in the divergent fluid path using a quantity charged particle radioactive detectors placed at locations along the second wall of the fluid channel, wherein at least one of the radioactive detectors is positioned to be in particle communication with at least one of the radioactive sources. As shown in block 706, operations further include but are not limited to estimating density of the fluid in the fluid channel based on a quantity of charged particles passing through the fluid in the fluid channel in at least one of the locations.

In other illustrative embodiments, a tool such as the charged particle densitometer described above may be used for permanent well monitoring. In these embodiments, the charged particle densitometer or at least a portion of the charged particle densitometer may be installed within a producing well to monitor production fluids. In some cases, producing wells may produce harmful compounds and/or gasses that may cause damage to equipment or present hazards at the well site. In one example, the method includes monitoring a producing well to estimate production fluid properties. The fluid properties may include the presence of harmful compounds such as hydrogen sulfide, carbonyl sulfide, cyanide, hydrogen cyanide, sulfur dioxide, and brine.

In at least one embodiment, one or more charged particle densitometers or at least a portion of the charged particle densitometers, as described and discussed above, may be used to periodically or continuously monitor production fluids. For example, one or more readings can be taken with at least one charged particle densitometer every 30 seconds, minute, two minutes, 5 minutes, one-half hour, hour, two hours, or any periodic interval desired. In another example, at least one charged particle densitometer can continually acquire data which can be processed in real time or stored and, if desired, later analyzed to provide a continuous monitoring of the production fluid as it is acquired.

In a particular embodiment, an apparatus is disclosed for estimating a property of a downhole fluid, the apparatus including but not limited to a carrier that is conveyable in a borehole; a test cell carried by the carrier for capturing the downhole fluid; a fluid channel immersed in the downhole fluid, the fluid channel having a first wall and a second wall, wherein the first wall faces the second wall; a quantity of charged particle sources placed at locations along the first wall of the fluid channel; and a quantity of charged particle detectors placed at locations along the second wall of the fluid channel, wherein each of the radioactive detectors is in positioned to be in particle communication with at least one of the charged particle sources.

In another embodiment of the apparatus, the apparatus further includes but is not limited to a positioner device in physical communication with at least one of the first wall and the second; and a processor configured to actuate the positioner device to change a distance between the first wall and the second wall to estimate density of the fluid in the fluid channel based on the quantity of charged particles detected passing through the downhole fluid in the fluid channel at the distance between the first wall and second wall. In another embodiment of the apparatus, the charged particle sources are alpha particle sources and the detectors are diamond alpha particle detectors. In another embodiment of the apparatus, the charged particle sources are selected from the group consisting of a monoenergetic particle sources and broad band particle sources.

In another embodiment of the apparatus, the apparatus further includes but is not limited to a non-stick coating rated to 300 degrees centigrade on the first wall and on the second wall of the fluid channel to reduce particles lodging in the fluid channel. In another embodiment of the apparatus, the fluid channel has a first end forming a first gap between the first wall and second wall approximately 5 microns wide and a second end forming a second gap between the first wall and second wall approximately 50 microns wide. In another embodiment of the apparatus, the apparatus further includes but is not limited to a calibration channel, having the same dimensions as the fluid channel, wherein the calibration channel is filled with a calibration medium.

In another embodiment of the apparatus, the fluid channel further comprises a constant depth fluid channel having a constant depth D wherein a first portion of the depth D of the fluid channel is filled with a calibration medium and a second portion of the depth D of the fluid channel is filled with the fluid, wherein each of a plurality charged particle sources further comprise a vertical array of charged particle sources, wherein at least one of the charged particle sources in a vertical array of charged particle sources is positioned to emit charged particles into the calibration medium at a location in the fluid channel and another one of the charged particle sources in another vertical array is positioned to emit charged particles into the fluid at another location in the fluid channel, and wherein each of the charged particle detectors further comprise a vertical array of charged particle detectors, wherein at least one of the charged particle detectors in a vertical array of charged particle detectors is positioned to detect charged particles passing through the calibration medium in the fluid channel at a first location and another one of the charged particle detectors in the vertical array is positioned to detect charged particles passing through the fluid at another location in the fluid channel.

In another embodiment a method is disclosed for estimating a property of a fluid downhole, the method including but not limited to conveying a test cell carried by the carrier for capturing a fluid downhole; emitting charged particles into the fluid downhole in a fluid channel immersed in the fluid downhole, the fluid channel having a first wall and a second wall, wherein the first wall faces the second wall and wherein the charged particles are emitted from at least one charged particle source placed at a location along the first wall of the fluid channel; and detecting the charged particles passing through the fluid in the fluid path using a quantity of charged particle detectors placed in locations along the second wall of the fluid channel, wherein at least one of the charged particle detectors is positioned to be in particle communication with at least one of the charged particle sources. In another embodiment of the method, the charged particle sources are alpha particle sources and the charged particle detectors are diamond detectors, the method further includes but is not limited to moving at least one of the first wall and second wall to change a width of the fluid channel; and estimating density of the fluid in the fluid channel based on a quantity of charged particles passing through the fluid in the fluid channel at a particular width of the fluid channel.

In another embodiment of the apparatus, the method further includes but is not limited to performing a least squares fit of charged particle detector measurements to determine the fluid density. In another embodiment of the apparatus, the charged particle sources are selected from the group consisting of a monoenergetic particle sources and broad band particle sources. In another embodiment of the apparatus, the fluid channel further includes but is not limited to a divergent width fluid channel, the method further includes but is not limited to emitting charged particles into the divergent width calibration channel downhole, the divergent width calibration channel having substantially the same dimensions as a divergent fluid channel, the calibration channel having a first wall and a second wall, wherein the first wall faces the second wall and is placed at a divergent angle relative to the second wall, wherein the charged particles are emitted form a quantity of charged particle sources placed at locations along the first wall of the calibration channel; detecting the charged particles passing through the calibration medium in the divergent calibration channel using a quantity of charged particle detectors placed in linear locations along the second wall of the calibration channel, wherein at least one of the charged particle detectors is in positioned to be in particle communication with at least one of the charged particle sources; and estimating density of the fluid in the fluid channel based on a quantity of charged particles passing through the fluid in the fluid channel and the calibration medium in the divergent calibration channel in at least one of the locations.

In another embodiment of the method, the charged particle source is a broadband charged particle source, the method further includes but is not limited to building up a distribution of energy level detections using multiple detection measurements along the divergent fluid channel and the divergent calibration channel. In another embodiment, a method is disclosed for estimating a property of a fluid downhole, the method including but not limited to emitting charged particles into the fluid downhole in a fluid channel immersed in the fluid downhole, the fluid channel having a first wall and a second wall, wherein the first wall faces the second wall, wherein the charged particles are emitted from a quantity of charged particle sources placed at locations along the first wall of the fluid channel; and detecting the charged particles passing through the fluid in the divergent fluid path using a quantity of charged particle detectors placed in locations along the second wall of the fluid channel, wherein each of the charged particle detectors is positioned to be in particle communication with at least one of the charged particle sources. In another embodiment of the method, the method further includes but is not limited to moving the at least one of the first wall and the second wall to change a width of the fluid channel; and estimating density of the fluid in the fluid channel based on a quantity of charged particles passing through the fluid in the fluid channel at a width of the fluid channel.

In another embodiment of the method, the method further includes but is not limited to performing a least squares fit of a plurality of charged particle detector measurements to determine the fluid density. In another embodiment of the method, the charged particle sources are selected from the group consisting of a mono energetic particle sources and broad band particle sources. In another embodiment of the method, the method further includes but is not limited to emitting charged particles into a divergent width calibration channel downhole, the divergent width calibration channel having substantially the same dimensions as the divergent fluid channel, the calibration channel having a first wall and a second wall, wherein the first wall faces the second wall and is placed at a divergent angle relative to the second wall, wherein the charged particles are emitted form a quantity, N of charged particle sources placed at locations 1 through N along the first wall of the calibration channel; detecting the charged particles passing through the calibration medium in the divergent calibration channel using a quantity, N of charged particle detectors placed in locations 1 through N along the second wall of the calibration channel, wherein each of the charged particle detectors 1 through N is in positioned to be in particle communication with a corresponding Nth one of the charged particle sources 1 through N; and estimating density of the fluid in the fluid channel based on a quantity of charged particles passing through the fluid in the fluid channel and the calibration medium in the divergent calibration channel in at least one of the locations, 1 through N.

Having described above the several aspects of the disclosure, one skilled in the art will appreciate several particular embodiments useful in determining a property of an earth subsurface structure using a downhole charged particle densitometer. The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

Given the above disclosure of general concepts and specific embodiments, the scope of protection is defined by the claims appended hereto. The issued claims are not to be taken as limiting Applicant's right to claim disclosed, but not yet literally claimed subject matter by way of one or more further applications including those filed pursuant to the laws of the United States and/or international treaty.

What is claimed is:

1. An apparatus for estimating a property of a downhole fluid, the apparatus comprising:
    a carrier that is conveyable in a borehole;
    a test cell carried by the carrier for capturing the downhole fluid;
    a fluid channel immersed in the downhole fluid, the fluid channel having a first wall and a second wall, wherein the first wall faces the second wall;
    a quantity of charged particle sources placed at locations along the first wall of the fluid channel;
    a quantity of charged particle detectors placed at locations along the second wall of the fluid channel, wherein each of the charged particle detectors is positioned to be in particle communication with at least one of the charged particle sources;
    and
    a positioner device in physical communication with at least one of the first wall and the second; and
    a processor configured to actuate the positioner device to change a distance between the first wall and the second wall to estimate density of the fluid in the fluid channel based on the quantity of charged particles detected passing through the downhole fluid in the fluid channel at the distance between the first wall and second wall.

2. The apparatus of claim 1, wherein the charged particle sources are alpha particle sources and the detectors are diamond alpha particle detectors.

3. The apparatus of claim 1, wherein the charged particle sources are selected from the group consisting of a monoenergetic particle sources and broad band particle sources.

4. The apparatus of claim 1, the apparatus further comprising:
    a non-stick coating rated to 300 degrees centigrade on the first wall and on the second wall of the fluid channel to reduce particles lodging in the fluid channel.

5. The apparatus of claim 1, wherein the fluid channel has a first end forming a first gap between the first wall and second wall approximately 5 microns wide and a second end forming a second gap between the first wall and second wall approximately 50 microns wide.

6. The apparatus of claim 1, the apparatus further comprising:
    a calibration channel, having the same dimensions as the fluid channel, wherein the calibration channel is filled with a calibration medium.

7. The apparatus of claim 5, wherein the fluid channel further comprises a constant depth fluid channel having a constant depth D wherein a first portion of the depth D of the fluid channel is filled with a calibration medium and a second portion of the depth D of the fluid channel is filled with the fluid, wherein each of a plurality charged particle sources further comprise a vertical array of charged particle sources, wherein at least one of the charged particle sources in a vertical array of charged particle sources is positioned to emit charged particles into the calibration medium at a location in the fluid channel and another one of the charged particle sources in another vertical array is positioned to emit charged particles into the fluid at another location in the fluid channel, and wherein each of the charged particle detectors further comprise a vertical array of charged particle detectors, wherein at least one of the charged particle detectors in a vertical array of charged particle detectors is positioned to detect charged particles passing through the calibration medium in the fluid channel at a first location and another one of the charged particle detectors in the vertical array is positioned to detect charged particles passing through the fluid at another location in the fluid channel.

8. A method for estimating a property of a fluid downhole, the method comprising:
    conveying a test cell carried by the carrier for capturing a fluid downhole;
    emitting charged particles into the fluid downhole in a fluid channel immersed in the fluid downhole, the fluid channel having a first wall and a second wall, wherein the first wall faces the second wall and wherein the charged particles are emitted from at least one charged particle source placed at a location along the first wall of the fluid channel; and
    detecting the charged particles passing through the fluid in the fluid path using a quantity of charged particle detectors placed in locations along the second wall of the fluid channel, wherein at least one of the charged particle detectors is positioned to be in particle communication with at least one of the charged particle sources, wherein the charged particle sources are alpha particle sources and the charged particle detectors are diamond detectors, the method further comprising:

moving at least one of the first wall and second wall to change a width of the fluid channel; and estimating density of the fluid in the fluid channel based on a quantity of charged particles passing through the fluid in the fluid channel at a particular width of the fluid channel.

9. The method of claim 8, the method further comprising:
performing a least squares fit of charged particle detector measurements to determine the fluid density.

10. The method of claim 8, wherein the charged particle sources are selected from the group consisting of a monoenergetic particle sources and broad band particle sources.

11. The method of claim 8, wherein the fluid channel further comprises a divergent width fluid channel, the method further comprising:

emitting charged particles into the divergent width calibration channel downhole, the divergent width calibration channel having substantially the same dimensions as a divergent fluid channel, the calibration channel having a first wall and a second wall, wherein the first wall faces the second wall and is placed at a divergent angle relative to the second wall, wherein the charged particles are emitted form a quantity of charged particle sources placed at locations along the first wall of the calibration channel;

detecting the charged particles passing through the calibration medium in the divergent calibration channel using a quantity of charged particle detectors placed in linear locations along the second wall of the calibration channel, wherein at least one of the charged particle detectors is in positioned to be in particle communication with at least one of the charged particle sources; and estimating density of the fluid in the fluid channel based on a quantity of charged particles passing through the fluid in the fluid channel and the calibration medium in the divergent calibration channel in at least one of the locations.

12. The method of claim 8, wherein the charged particle source is a broadband charged particle source, the method further comprising:

building up a distribution of energy level detections using multiple detection measurements along the divergent fluid channel and the divergent calibration channel.

13. A method for estimating a property of a fluid downhole, the method comprising:

emitting charged particles into fluid downhole in a fluid channel immersed in the fluid downhole, the fluid channel having a first wall and a second wall, wherein the first wall faces the second wall, wherein the charged particles are emitted from a quantity of charged particle sources placed at locations along the first wall of the fluid channel;

detecting the charged particles passing through the fluid in the divergent fluid path using a quantity of charged particle detectors placed in locations along the second wall of the fluid channel, wherein each of the charged particle detectors is positioned to be in particle communication with at least one of the charged particle sources;

moving the at least one of the first wall and the second wall to change a width of the fluid channel; and estimating density of the fluid in the fluid channel based on a quantity of charged particles passing through the fluid in the fluid channel at a width of the fluid channel.

14. The method of claim 13, the method further comprising:

performing a least squares fit of a plurality of charged particle detector measurements to determine the fluid density.

15. The method of claim 13, wherein the charged particle sources are selected from the group consisting of a mono energetic particle sources and broad band particle sources.

16. The method of claim 13, the method further comprising:

emitting charged particles into a divergent width calibration channel downhole, the divergent width calibration channel having substantially the same dimensions as the divergent fluid channel, the calibration channel having a first wall and a second wall, wherein the first wall faces the second wall and is placed at a divergent angle relative to the second wall, wherein the charged particles are emitted form a quantity, N of charged particle sources placed at locations 1 through N along the first wall of the calibration channel;

detecting the charged particles passing through the calibration medium in the divergent calibration channel using a quantity, N of charged particle detectors placed in locations 1 through N along the second wall of the calibration channel, wherein each of the charged particle detectors 1 through N is in positioned to be in particle communication with a corresponding Nth one of the charged particle sources 1 through N; and estimating density of the fluid in the fluid channel based on a quantity of charged particles passing through the fluid in the fluid channel and the calibration medium in the divergent calibration channel in at least one of the locations, 1 through N.

* * * * *